(12) United States Patent
Miglis (10) Patent No.: US 11,035,840 B2
(45) Date of Patent: Jun. 15, 2021

(54) METHOD FOR PROCESSING A FLUID

(71) Applicant: ELITE HOLDING SOLUTIONS, LLC, Taft, CA (US)

(72) Inventor: Robert A. Miglis, Bakersfield, CA (US)

(73) Assignee: Elite Holding Solutions, LLC, Taft, CA (US)

( * ) Notice: Subject to any disclaimer, the term of this patent is extended or adjusted under 35 U.S.C. 154(b) by 287 days.

(21) Appl. No.: 16/387,776

(22) Filed: Apr. 18, 2019

(65) Prior Publication Data

US 2019/0324011 A1 Oct. 24, 2019

Related U.S. Application Data

(60) Provisional application No. 62/659,621, filed on Apr. 18, 2018.

(51) Int. Cl.
| | |
|---|---|
| *G01N 33/28* | (2006.01) |
| *G01N 1/40* | (2006.01) |
| *E21B 49/08* | (2006.01) |
| *B01D 19/00* | (2006.01) |
| *E21B 43/34* | (2006.01) |

(52) U.S. Cl.
CPC ..... *G01N 33/2847* (2013.01); *B01D 19/0042* (2013.01); *E21B 43/34* (2013.01); *E21B 49/086* (2013.01); *G01N 1/4077* (2013.01); *E21B 49/0875* (2020.05)

(58) Field of Classification Search
CPC .. G01N 33/2847; E21B 43/34; E21B 49/0875
See application file for complete search history.

(56) References Cited

U.S. PATENT DOCUMENTS

| | | | | |
|---|---|---|---|---|
| 1,350,576 | A * | 8/1920 | Smith | E21B 43/34 |
| | | | | 96/159 |
| 1,515,126 | A * | 11/1924 | Lennox | E21B 43/34 |
| | | | | 96/159 |
| 2,049,578 | A * | 8/1936 | Werts | E21B 43/34 |
| | | | | 96/159 |
| 2,574,116 | A | 11/1951 | Loumiet et Lavigne | |
| 2,925,720 | A * | 2/1960 | Dorsey | E21B 43/34 |
| | | | | 62/633 |
| 3,025,928 | A * | 3/1962 | Heath | E21B 43/34 |
| | | | | 95/18 |
| 4,342,572 | A * | 8/1982 | Heath | B01D 3/00 |
| | | | | 96/173 |

(Continued)

*Primary Examiner* — John Fitzgerald
(74) *Attorney, Agent, or Firm* — Rao DeBoer Osterrieder, PLLC; John M. DeBoer (57) ABSTRACT

A method for processing a fluid that includes receiving the fluid into a testing skid as an inlet flow, the fluid comprising a multi-phase fluid produced from a well. The method includes controlling the inlet flow in a manner whereby an at least a portion of the inlet flow is transferred as a diverted stream to a separation component associated with the testing skid, and using the separation component to restructure an at least a portion of the diverted stream into stratified flow regimes. The stratified flow regimes entail a gas phase and a liquid phase. The method includes using the water cut meter to determine a water:oil ratio present in the liquid phase; and discharging the liquid phase from the testing skid.

15 Claims, 5 Drawing Sheets

(56) References Cited

U.S. PATENT DOCUMENTS

| | | | | |
|---|---|---|---|---|
| 5,004,552 A * | | 4/1991 | Al-Yazdi | B01D 17/0208 210/789 |
| 7,311,001 B2 * | | 12/2007 | Liu | B01D 17/0211 73/215 |
| 7,434,621 B2 * | | 10/2008 | Aarvik | E21B 43/00 166/267 |
| 7,681,444 B2 * | | 3/2010 | Raskie | G01N 9/002 73/200 |
| 9,346,688 B2 * | | 5/2016 | Andreussi | E21B 43/36 |
| 9,410,422 B2 * | | 8/2016 | Sondhi | E21B 49/008 |
| 9,863,798 B2 * | | 1/2018 | Henry | G01F 1/8468 |
| 10,139,257 B2 * | | 11/2018 | Ahmad | G01F 1/74 |
| 10,180,056 B2 * | | 1/2019 | Mashetty | E21B 43/12 |
| 10,478,753 B1 * | | 11/2019 | Elms | E21B 43/26 |
| 2007/0204750 A1 * | | 9/2007 | Liu | G01F 1/74 96/182 |
| 2008/0307891 A1 * | | 12/2008 | Raskie | E21B 47/10 73/861.04 |
| 2013/0247684 A1 * | | 9/2013 | Suda | E21B 43/34 73/861.04 |
| 2014/0137642 A1 * | | 5/2014 | Henry | G01F 1/84 73/152.29 |
| 2014/0137643 A1 * | | 5/2014 | Henry | G01F 1/84 73/152.31 |
| 2015/0027730 A1 * | | 1/2015 | Hall | E21B 33/038 166/379 |
| 2015/0034570 A1 * | | 2/2015 | Andreussi | C02F 1/40 210/801 |
| 2015/0185062 A1 * | | 7/2015 | Ahmad | G01F 15/08 73/861.04 |
| 2016/0215618 A1 * | | 7/2016 | Marshal | E21B 21/067 |
| 2016/0273950 A1 * | | 9/2016 | Henry | E21B 47/00 |
| 2017/0122097 A1 * | | 5/2017 | Suheil | E21B 47/10 |
| 2017/0122100 A1 * | | 5/2017 | Mashetty | E21B 43/34 |
| 2017/0167906 A1 * | | 6/2017 | Henry | E21B 21/063 |
| 2017/0219403 A1 * | | 8/2017 | Henry | G01F 15/005 |
| 2017/0306720 A1 * | | 10/2017 | Hall | E21B 33/038 |
| 2017/0342824 A1 | | 11/2017 | Marshall | |
| 2018/0275111 A1 * | | 9/2018 | Stolle | E21B 49/088 |
| 2019/0049279 A1 * | | 2/2019 | Ahmad | G01F 1/74 |
| 2019/0136681 A1 * | | 5/2019 | Mashetty | E21B 43/12 |
| 2019/0324011 A1 * | | 10/2019 | Miglis | B01D 17/0217 |
| 2020/0224529 A1 * | | 7/2020 | Suheil | E21B 47/103 |
| 2020/0324224 A1 * | | 10/2020 | Allouche | C02F 1/40 |

* cited by examiner

METHOD FOR PROCESSING A FLUID

BACKGROUND

Field of the Disclosure

This disclosure generally relates to methods and systems, and related units, for processing a fluid. Processing the fluid may include obtaining test or measurement data that may be used and beneficial for any number of reasons, such as to determine well performance. Particular embodiments herein relate to removing or separating one or more phases, constituents, and the like, from a production fluid at, or proximately close to, a wellhead in an expedient manner so that the resultant separated phases may be quickly and accurately tested or measured. Other embodiments pertain to restructuring flow regimes of a fluid in a manner whereby a particular fluid phase or component in a flow stream may be predictably and reliably located in a certain area of the flow stream, which allows for effective separation of the various components of the fluid, followed by testing or measuring, and in some instances recombining.

Background of the Disclosure

A hydrocarbon-based economy continues to be a dominant force in the modern world. As such, locating and producing hydrocarbons continues to demand attention from the oil and gas (O&G) industry. Once hydrocarbons have been found, a well is formed in a surrounding formation so that valuable fluids therein may be produced, and later refined into commercial products, such as gasoline or natural gas.

Figure 1:
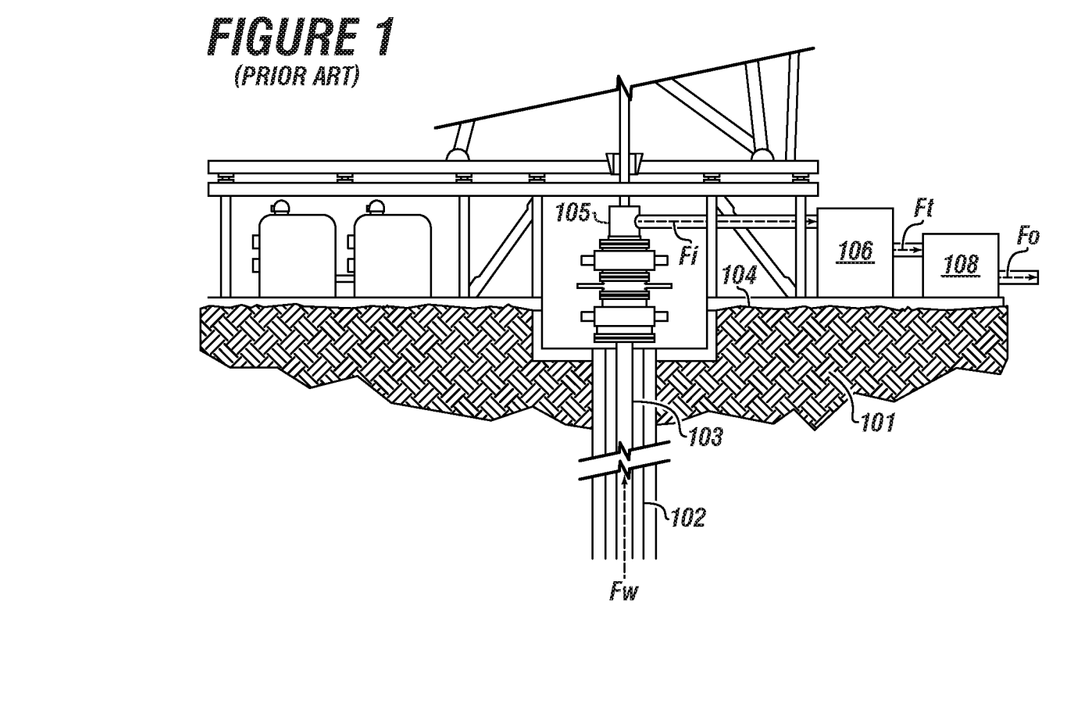
FIG. 1 shows an overview process diagram of a conventional production process.

FIG. 1 illustrates a conventional production process, which includes a well or wellbore 102 formed in a surrounding formation 101. The well 102 may include vertical, horizontal, or mixed orientation, with optimizing production being the driver. Once the well 102 is completed, a production tube 103 is installed, with a cap or wellhead 105 placed thereon. Fluids Fw from the wellbore may then be produced to the surface (or surface facility) 104.

Producers/operators need to be able to test the well 102 in the sense of what it is producing, so accurate measurement of what is coming out is paramount. Oftentimes well production is tied to some kind of royalty payment for mineral rights, so it can be critical to know with precision what minerals, and in what percentage, are present in the fluid Fw. In other instances, engineers or operators need to know how efficient the well is producing, which is often based on the amount and type of hydrocarbon being produced (e.g., oil, natural gas, etc.) versus other constituents.

Fluids Fw may be 3- or 4-phase, and may include various solids, organics, aqueous, and gases. The gas may be entrained. A multiphase fluid includes a mixture of different fluids having different phases, such as air and water, steam and water, or oil and natural gas. Moreover, the liquid phase may further comprise different liquid components, such as oil and water. A gas-liquid two phase flow takes many different forms and may be classified into various types of gas distribution within the liquid, which may be referred to as flow regimes or flow patterns.

As the fluid Fw leaves the well 102, an initial portion (or all) of it (e.g., Fluid Fi) may be diverted for testing (which may be real-time and in-line). Traditional testing often includes some kind of separation unit operation, usually in the form of a 3-phase vertical or horizontal gravity separator 106. The process of separation in a gravity separator is primarily the function of differences in density, where gas rises to the top and out of the liquid phase, and the oily layer sits on top of the heavier aqueous layer. A sample from one or all of these constituents is then taken and tested. For example, separated fluid (or portion thereof) Ft is then transferred to a testing unit 108, with a separated, tested fluid Fo transferred out of the process.

This type of separation not only requires large retention times, but is also never full proof, as inevitably the gas remains entrained, the liquid contains gas bubbles, and so forth. But meters on on the market can measure only liquid or only gas. So when a gas stream has liquid, and/or a liquid stream has gas, the accuracy of the testing result is inaccurate, and all too frequently substantially inaccurate.

There is a need in the art for fast, cheap, and efficient separation of a multiphase fluid, followed by accurate and effective measurement of resultant, separated product streams. There is a need in the art to form distinct flow regimes within a given fluid.

There is a need for an improved separation and testing process that have any of low operating costs, reduced capital costs, safe to use, compact footprint, and substantial or complete separation of phases of a fluid. There is a need in the art for equipment units that may be retrofitted or coupled with any existing facility.

SUMMARY

Embodiments herein pertain to a method for processing a fluid that may include the step of receiving the fluid into a testing skid as an inlet flow, the fluid comprising a multiphase fluid. The method may include controlling the inlet flow in a manner whereby an at least a portion of the inlet flow is transferred as a diverted stream to a separation component associated with the testing skid.

The method may include determining a first parameter of the diverted stream. The method may include using the separation component to restructure an at least a portion of the diverted stream into stratified flow regimes comprising one or both of a gas phase and a liquid phase. The method may include transferring the liquid phase from the separation component to a liquid meter loop. The meter loop may include a flow meter and a water cut meter.

The method may include operating the liquid meter loop to determine a plurality of parameters. In aspects, a flow rate and a percent of water of the liquid phase may be determined.

The method may include providing information associated with a first parameter and the plurality of parameters to the water cut meter. The method may further include using the water cut meter to determine a water:oil ratio present in the liquid phase. The method may include discharging the liquid phase from the testing skid.

After stratifying, the (separated) gas phase may include greater than 99% by weight gas. The (separated) liquid phase may include greater than 99% by weight liquid. There may be an average bulk residence time of the at least a portion of the diverted stream in the separation unit of less than 5 minutes.

In aspects, the liquid meter may be arranged vertically. Accordingly, the liquid phase may enter a bottom of the liquid meter and exit a top of the liquid meter.

The method may include reinjecting the gas phase into the liquid phase to form a recombined stream that is then subject to the discharging step. In aspects, the separation component may be an external winding helically wound in a horizontal orientation. The external winding may include between 2 to 10 coil loops. The external winding may be formed around or be part of a separation unit.

The diverted stream may have an average bulk fluid velocity through the separation component between 0.1 feet per second to 15 feet per second.

Still other embodiments of the disclosure pertain to a method for processing a fluid that may include the step of receiving the fluid into a testing skid as an inlet flow. The fluid may be a multi-phase fluid transferred from a fluid source.

The method may include controlling the inlet flow in a manner whereby an at least a portion of the inlet flow is transferred as a diverted stream to a separation component or unit. The component or unit may be or otherwise include an external winding associated with the testing skid. The external winding may include between 2 to 10 coil loops disposed around a separator vessel.

The method may include determining a first parameter of the diverted stream. The method may include using the separation component to restructure an at least a portion of the diverted stream into flow regimes comprising a gas phase and a liquid phase. The method may include transferring the liquid phase from a winding outlet of the external winding to a liquid meter loop comprising a flow meter and a water cut meter.

The method may include operating the liquid meter loop to determine a plurality of parameters. In aspects, a flow rate and a percent of water of the liquid phase may be determined. The method may include providing a set of data associated with a first parameter and the plurality of parameters to the water cut meter.

The method may include using the water cut meter to determine a water:oil ratio present in the liquid phase; and discharging the liquid phase from the testing skid.

These and other embodiments, features and advantages will be apparent in the following detailed description and drawings.

BRIEF DESCRIPTION OF THE DRAWINGS

A full understanding of embodiments disclosed herein is obtained from the detailed description of the disclosure presented herein below, and the accompanying drawings, which are given by way of illustration only and are not intended to be limitative of the present embodiments, and wherein.

DETAILED DESCRIPTION

Regardless of whether presently claimed herein or in another application related to or from this application, herein disclosed are novel apparatuses, units, systems, and methods that pertain to improved fluid processing, which may include separation, testing, and aspects related thereto, details of which are described herein.

Embodiments of the present disclosure are described in detail with reference to the accompanying Figures. In the following discussion and in the claims, the terms "including" and "comprising" are used in an open-ended fashion, such as to mean, for example, "including, but not limited to . . . ". While the disclosure may be described with reference to relevant apparatuses, systems, and methods, it should be understood that the disclosure is not limited to the specific embodiments shown or described. Rather, one skilled in the art will appreciate that a variety of configurations may be implemented in accordance with embodiments herein.

Although not necessary, like elements in the various figures may be denoted by like reference numerals for consistency and ease of understanding. Numerous specific details are set forth in order to provide a more thorough understanding of the disclosure; however, it will be apparent to one of ordinary skill in the art that the embodiments disclosed herein may be practiced without these specific details. In other instances, well-known features have not been described in detail to avoid unnecessarily complicating the description. Directional terms, such as "above," "below," "upper," "lower," "front," "back," etc., are used for convenience and to refer to general direction and/or orientation, and are only intended for illustrative purposes only, and not to limit the disclosure.

Connection(s), couplings, or other forms of contact between parts, components, and so forth may include conventional items, such as lubricant, additional sealing materials, such as a gasket between flanges, PTFE between threads, and the like. The make and manufacture of any particular component, subcomponent, etc., may be as would be apparent to one of skill in the art, such as molding, forming, press extrusion, machining, or additive manufacturing. Embodiments of the disclosure provide for one or more components to be new, used, and/or retrofitted to existing machines and systems.

Various equipment may be in fluid communication directly or indirectly with other equipment. Fluid communication may occur via one or more transfer lines and respective connectors, couplings, valving, piping, and so forth. Fluid movers, such as pumps, may be utilized as would be apparent to one of skill in the art.

Numerical ranges in this disclosure may be approximate, and thus may include values outside of the range unless otherwise indicated. Numerical ranges include all values from and including the expressed lower and the upper values, in increments of smaller units. As an example, if a compositional, physical or other property, such as, for example, molecular weight, viscosity, melt index, etc., is from 100 to 1,000. it is intended that all individual values, such as 100, 101, 102, etc., and sub ranges, such as 100 to 144, 155 to 170, 197 to 200, etc., are expressly enumerated. It is intended that decimals or fractions thereof be included. For ranges containing values which are less than one or containing fractional numbers greater than one (e.g., 1.1, 1.5, etc.), smaller units may be considered to be 0.0001, 0.001, 0.01, 0.1, etc. as appropriate. These are only examples of what is specifically intended, and all possible combinations of numerical values between the lowest value and the highest value enumerated, are to be considered to be expressly stated in this disclosure. Numerical ranges are provided within this disclosure for, among other things, the relative amount of reactants, surfactants, catalysts, etc. by itself or in a mixture or mass, and various temperature and other process parameters.

Terms

The term "connected" as used herein may refer to a connection between a respective component (or subcomponent) and another component (or another subcomponent), which can be fixed, movable, direct, indirect, and analogous to engaged, coupled, disposed, etc., and can be by screw, nut/bolt, weld, and so forth. Any use of any form of the terms "connect", "engage", "couple", "attach", "mount", etc. or any other term describing an interaction between elements is not meant to limit the interaction to direct interaction between the elements and may also include indirect interaction between the elements described.

The term "fluid" as used herein may refer to a liquid, gas, slurry, single phase, multi-phase, pure, impure, etc. and is not limited to any particular type of fluid such as hydrocarbons.

The term "fluid connection", "fluid communication," "fluidly communicable," and the like, as used herein may refer to two or more components, systems, etc. being coupled whereby fluid from one may flow or otherwise be transferrable to the other. The coupling may be direct, indirect, selective, alternative, and so forth. For example, valves, flow meters, pumps, mixing tanks, holding tanks, tubulars, separation systems, and the like may be disposed between two or more components that are in fluid communication.

The term "pipe", "conduit", "line", "tubular", or the like as used herein may refer to any fluid transmission means, and may be tubular in nature.

The term "composition" or "composition of matter" as used herein may refer to one or more ingredients, components, constituents, etc. that make up a material (or material of construction). Composition may refer to a flow stream of one or more chemical components.

The term "chemical" as used herein may analogously mean or be interchangeable to material, chemical material, ingredient, component, chemical component, element, substance, compound, chemical compound, molecule(s), constituent, and so forth and vice versa. Any 'chemical' discussed in the present disclosure need not refer to a 100% pure chemical. For example, although 'water' may be thought of as H2O, one of skill would appreciate various ions, salts, minerals, impurities, and other substances (including at the ppb level) may be present in 'water'. A chemical may include all isomeric forms and vice versa (for example, "hexane", includes all isomers of hexane individually or collectively).

The term "water" as used herein may refer to a pure, substantially pure, and impure water-based stream, and may include waste water, process water, fresh water, seawater, produced water, slop water, treated variations thereof, mixes thereof, etc., and may further include impurities, dissolved solids, ions, salts, minerals, and so forth. Water for a frac fluid can also be referred to as 'frac water'.

The term "produced water" as used herein may refer to water recovered from a subterranean formation or other area near the wellbore. Produced water may include flowback water, brine, salt water, or formation water. Produced water may include water having dissolved and/or free organic materials. Produced water may refer to water from non-wellbore related processes, such as potable water treatment, sewage treatment, and equipment and building maintenance.

The term "treatment" (or treating, treated, treat, etc.) as used herein may refer to an action or act such as purifying, separating, charging, heating, drying, cleaning, and so forth. One example may include 'treating' a multi-phase fluid to separate phases. Another example may include 'treating' a substantially aqueous (water) stream to remove a non-aqueous component. The act may be the result of an automated or manually controlled piece of equipment working separately or in combination with other components.

The term "testing" as used herein may refer to an action such as testing or measuring a material, such a fluid, to determine its composition or makeup. The act may be the result of an automated or manually controlled piece of equipment working separately or in combination with other components. For example, a liquid phase of a fluid may be tested to determine a water:oil ratio of the liquid phase.

The term "impurity" as used herein may refer to an undesired component, contaminant, etc. of a composition. For example, a hydrocarbon or organic component may be an impurity of a water stream. As another example, in testing a liquid phase stream, an impurity may be gas bubbles entrained in the liquid phase.

The term "skid" as used herein may refer to one or more pieces of equipment operable together for a particular purpose. For example, a 'well tester skid' may refer to one or more pieces of equipment operable to provide or facilitate a testing process related to a well. A skid may be mobile, portable, or fixed. Although 'skid' may refer to a modular arrangement of equipment, as used herein may be mentioned merely for a matter of brevity and simple reference, with no limitation meant. Thus, skid may be comparable or analogous to zone, system, subsystem, and so forth.

The term "skid mounted" as used herein may refer to one or more pieces operable together for a particular purpose that may be associated with a frame- or skid-type structure. Such a structure may be portable or fixed.

The term "utility fluid" as used herein may refer to a fluid used in connection with the operation of a heat generating device, such as a lubricant or water. The utility fluid may be for heating, cooling, lubricating, or other type of utility. 'Utility fluid' can also be referred to and interchangeable with 'service fluid' or comparable.

The term "mounted" as used herein may refer to a connection between a respective component (or subcomponent) and another component (or another subcomponent), which can be fixed, movable, direct, indirect, and analogous to engaged, coupled, disposed, etc., and can be by screw, nut/bolt, weld, and so forth.

The term "sensor" as used herein can refer to a device that detects or measures a physical property and may record, indicate, or otherwise respond to it. The output of a sensor can be an analog or digital signal.

The term "microprocessor" as used herein can refer to a logic chip or a computer processor on a microchip. The microprocessor may have most or all central processing unit (CPU) functions.

The term "microcontroller", "programmable logic controller", "PLC", and the like, as used herein can refer to a CPU with additional function or structure, such as RAM, ROM, and or peripherals like I/O all embedded on a single chip.

The term "computer readable medium" (CRM) as used herein can refer to any type of medium that can store programming for use by or in connection with an instruction execution system, apparatus, or device. The CRM may be, for example, a device, apparatus, or system based on electronic, magnetic, optical, electromagnetic, or semiconductor function. By way of further example, the CRM may include an electrical connection (electronic) having one or more wires, a portable computer diskette (magnetic or optical), a random access memory (RAM) (electronic), a read-only memory (ROM) (electronic), an erasable programmable read-only memory (EPROM, EEPROM, or Flash memory)

(electronic), an optical fiber (optical), and a portable compact disc memory (CDROM, CD R/W) (optical).

The term "Wi-Fi module" as used herein can refer to a device or logic circuit that provides ability for a microcontroller to communicate data to a network, as well as update firmware and code inside the microcontroller.

Figure 2:
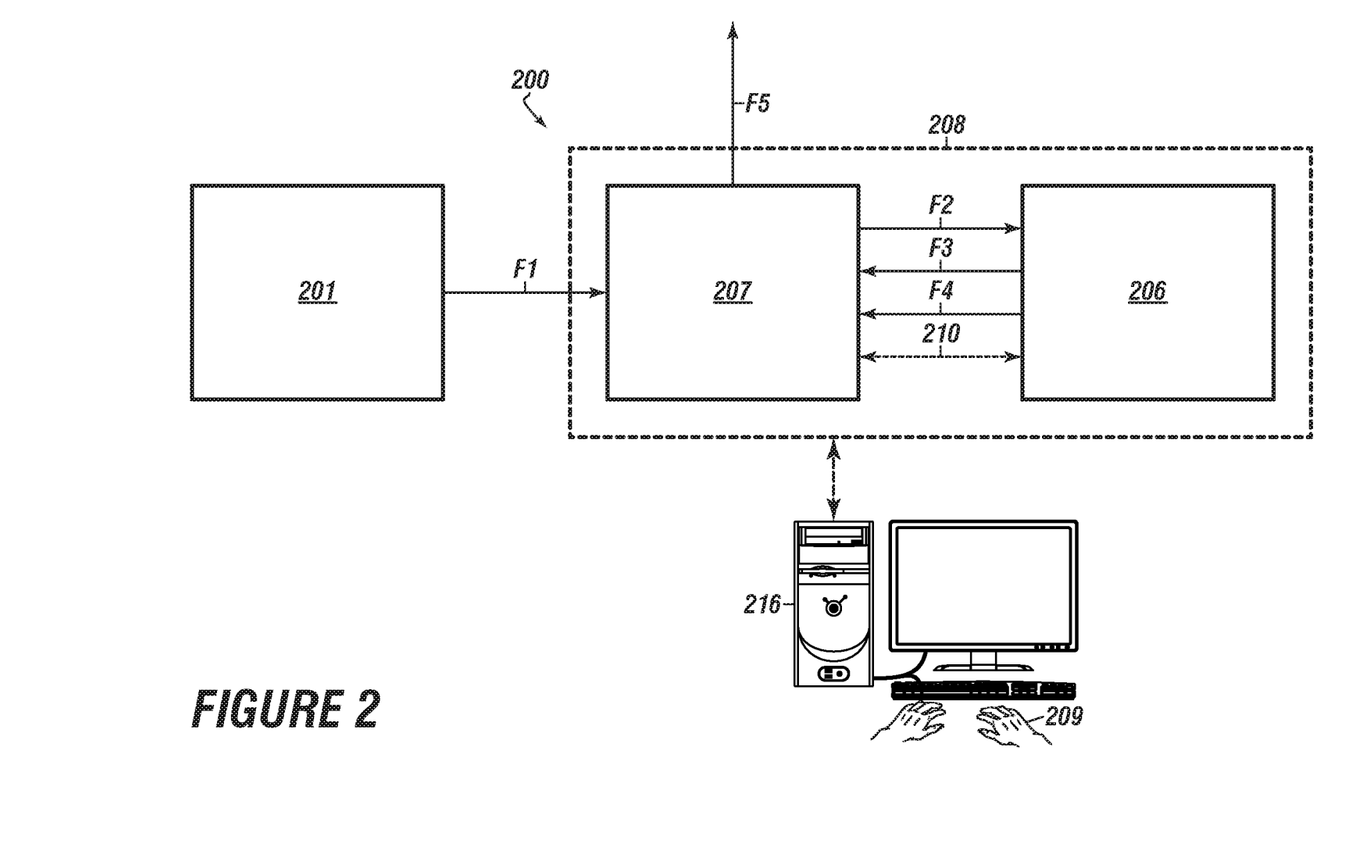
FIG. 2 shows an overview diagram of a system for processing a fluid according to embodiments of the disclosure.

Referring now to FIG. 2, an overview diagram of a system for processing a fluid, in accordance with embodiments disclosed herein, is shown. System 200 may include one or more components (or subcomponents) coupled with existing equipment. System 200 may include one or more units that are skid mounted or may be a collection of skid units. System 200 may be suitable for onshore and offshore environments.

Although not shown here, the system 200 may include a separation/testing unit or skid 208. The skid 208 may have various valves, flanges, pipes, pumps, utilities, monitors, sensors, controllers, flow meters, safety devices, etc., for accommodating sufficient universal coupling between the skid 208 and any applicable feedline/feed source of a fluid to be treated from a source operation 201.

The skid 208 may be in fluid communication with a wellbore, wellhead, operating system, production system, tank etc. associated with the source operation 201. The source of fluid may also be a natural or free-standing source, such as a pond (natural or manmade), a lagoon, lake, river, etc. The skid 208 may include a monitoring unit 216 operable to ensure the fluid stream F1 is suitable for the skid 208. The monitoring unit 216 may include various instrumentation and data transfer capability. The monitoring unit 216 may be programmable for automation and/or be operable via an operator 209.

The skid 208 may have a return or bypass line (not shown here) for in the event the fluid stream F1 may be deemed unsuitable, and thus the fluid stream may be transferred elsewhere from the system 200. Provided the fluid F1 meets predetermined specification, the fluid may transfer into the skid 208 for further processing.

The components of the skid 208 may be mounted to a frame-type structure via one or more legs, support mounts, etc. or otherwise positioned on a flooring. It is noted that while the separator or tester units (or sections) 206, 207 may be referred to as part of a 'skid' for simplicity, components of the skid 208 need not be skid mounted. The skid 208 may be part of the system 200. While it need not be exactly the same, system 200 and tester skid 208 may include various features and components like that of other systems or units described herein, and thus components thereof may be duplicate or analogous.

Fluid $F_1$ may be received into the skid and upon processing, may leave as a 'processed fluid' $F_5$. 'Processed' is not meant be limited, as this may include reference to treated, tested, measured, sensed, transferred, separated, combinations, etc. in whatever manner may be desired or applicable for system 200 (300, etc.). It is noted that while various steps or operations of the system 200 may be described in a sequential manner, the system 200 may be operated in batch or continuous fashion.

The system 200 may include various piping and valving associated with respective controller logic. Thus, the system 200 may include and be operatively associated with a programmable logic controller (PLC) (not shown here). The PLC may be configured or associated with a computer readable medium having computer instructions associated therewith. Although details of wiring and other instrumentation are not shown here, one of skill in the art would appreciate multiple inputs may be associated with the PLC. Inputs may pertain to data transmitted from a source(s), such as a sensor(s) associated with another piece(s) of equipment.

One or more parameters associated with the skid 208 may be monitored, detected, measured, sensed, etc. For example, pressure and temperature of the fluid F1 may be monitored by sensor transmitters. This may ensure the fluid F1 has respective properties (e.g., pressure and temperature) within tolerance levels of the equipment of the skid 208. Any tolerance level may be predetermined.

Provided that fluid F1 enters the skid 208 for processing, all or portions of the fluid F1 may be transferred via interconnected fluid transfer mechanisms, such as piping, to a separation section 206, as shown by fluid flow line F2.

The separation section 206 may be configured to reconfigured flow regimes associated with fluid F2 to the degree of forming separated fluids F3, F4. Fluid F3 may be substantially liquid phase, and F4 may be substantially gas phase. Either or both of fluids F3, F4 may be returned or transferred to the testing section 207 for further processing. Other fluids may be directly discharged from the separation section 207 or skid 208. A fluid may include a liquid phase and a vapor phase, which may be—but need not be— referred to as distinct or different fluids.

Of significance, measurement data from respective meters (and associated sensors and instrumentation) may be transmitted to the PLC. Measurement data may include, but not be limited to, density and/or volume, conductivity, pressure, temperature, etc., any of which may be transmitted to the PLC from each respective device. The PLC may then process and/or send combined data in a manner that may beneficially result in real time compensation to the values provided by devices, and compensate for any liquid property changes.

Once processed, fluids F3 and F4 may be (re)combined, and either or both discharged from the system 200 as shown by fluid arrow F5.

Figure 3A:
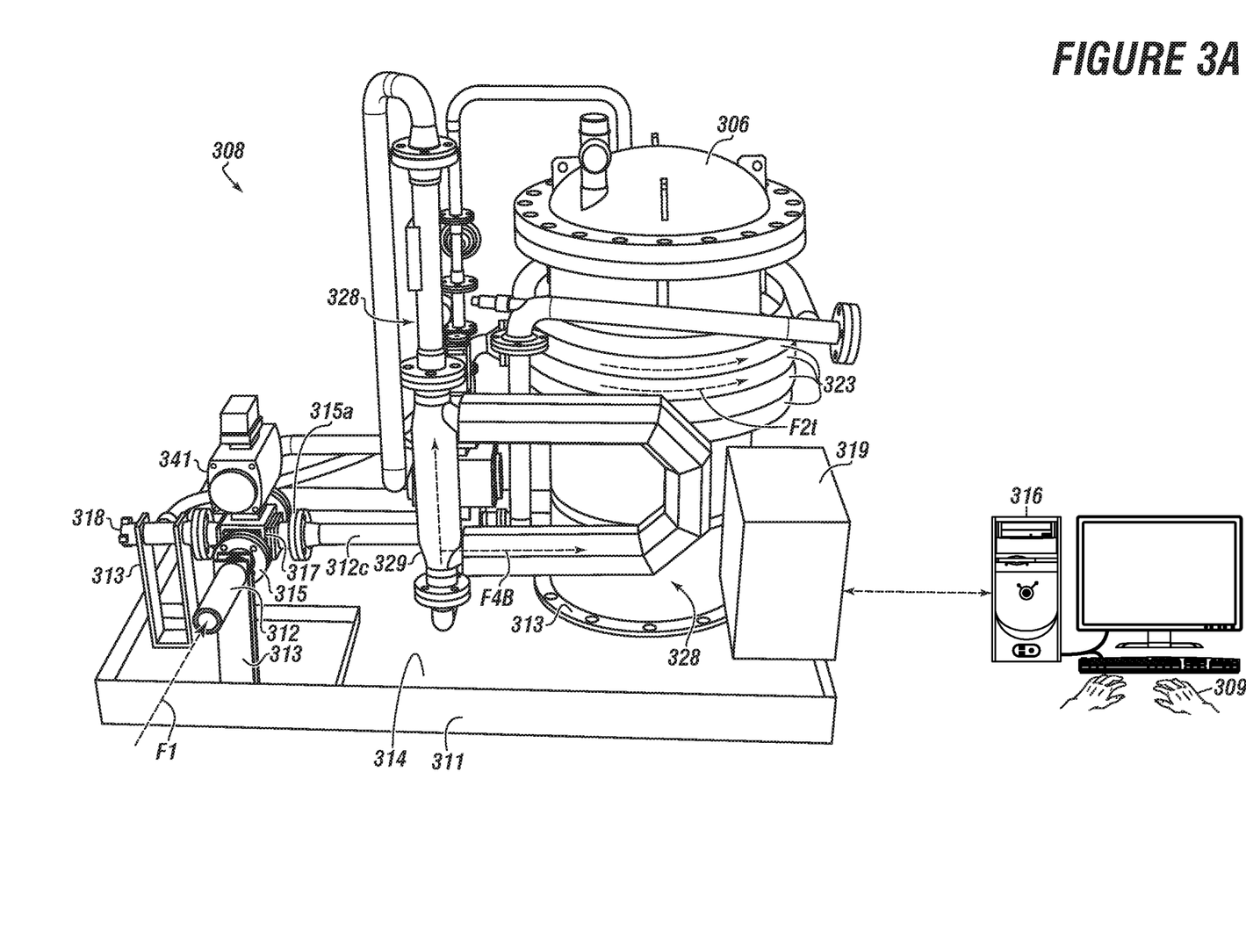
FIG. 3A shows a first side view of system operable to process a fluid according to embodiments of the disclosure.
Figure 3B:
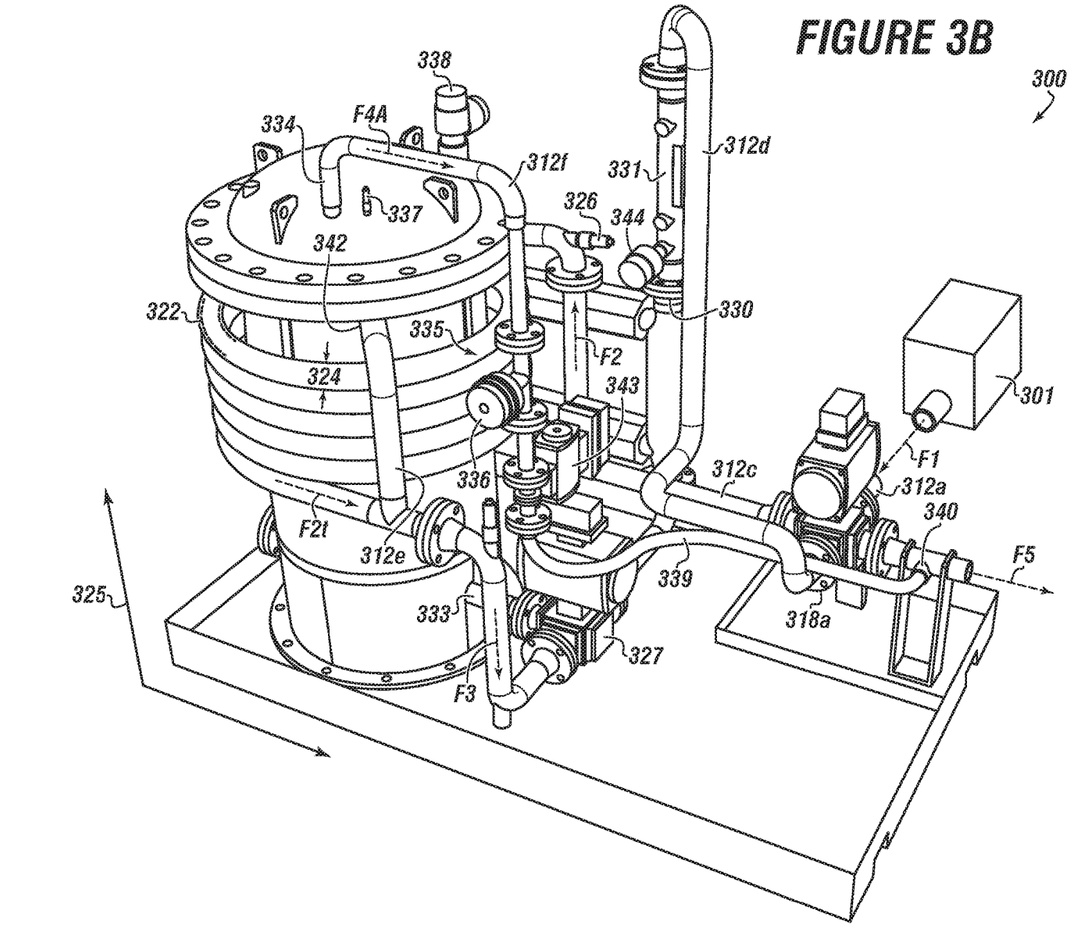
FIG. 3B shows a second side view of the system of FIG. 3A according to embodiments of the disclosure.

Referring now to FIGS. 3A and 3B, which together illustrate a tester skid 308 usable with system and process embodiments described herein. The components, piping, sensors, meters, etc. shown may be part of an overall fluid processing system 300. Embodiments herein apply to the tester skid 308 that may be an inclusive assembly of a number of components, subcomponents, etc. which may be further associated with operable systems, subsystems, assemblies, modules, skids and so forth, including those described herein. In embodiments there may be a single or a plurality skids, which may be operable in series, parallel, or as may otherwise be desired.

The components of the skid 308 may be mounted to a frame-type structure 311 via one or more legs, support mounts, etc. 313 or otherwise positioned on a flooring 314. It is noted that while the separator or tester units (or sections) 306, 307 may be referred to as part of a 'skid' for simplicity, components of the skid 308 need not be skid mounted. The skid 308 may be part of an overall system, such as system 300. While it need not be exactly the same, system 300 and tester skid 308 may include various features and components like that of other systems or units described herein, and thus components thereof may be duplicate or analogous.

The skid 308 may be configured to interface or couple with a unit, operation, system, etc. whereby an incoming fluid F1 received from, for example, a source 301. Shown here only in representative 'black box' form, the source 301 may be, for example, a pre-treatment vessel, another skid, or a well (or wellhead, wellbore, etc.).

Fluid $F_1$ may be received into the skid 308 from the source 301 via an inlet 312a, and upon processing, may leave the via an outlet 318 (or associated outlet piping) as a 'processed fluid' $F_5$. 'Processed' is not meant be limited, as this may include reference to treated, tested, measured, sensed, transferred, separated, combinations, etc. in whatever manner may be desired or applicable for system 300.

As shown in FIGS. 3A-3B together, the inlet fluid F1 may enter the testing section 307 of the skid 308 unit through inlet piping 312a. It is noted that while various steps or operations of the system 300 may be described in a sequential manner, the system 300 may be operated in batch or continuous fashion.

The inlet 315 (or inlet piping 312a) may be coupled or otherwise in fluid communication with an inlet valve 317. The inlet valve 317 may be a diverter valve. In embodiments, the inlet valve 317 may be a 4-way diverter valve. The inlet valve 317 may be configured for controlling and directing flow into and out of the skid 308. In a bypass mode, the inlet valve 317 may be configured to divert or otherwise bypass flow F1 into (briefly) and out of a skid outlet 318. The skid outlet 318 (or outlet piping) may be coupled or otherwise in fluid communication with the inlet valve 317. The inlet valve 317 may have an associated actuator 341. Analogously other valves of skid 308 may have an associated actuator, even if not shown or described.

The inlet valve 317 may be operatively associated with a programmable logic controller (PLC) 319. The PLC 319 may be configured or associated with a computer readable medium having computer instructions associated therewith. Although details of wiring and other instrumentation are not shown here, one of skill in the art would appreciate multiple inputs may be associated with the PLC 319. Inputs may pertain to data transmitted from a source(s), such as a sensor(s) associated with another piece(s) of equipment.

The PLC 319 may be any suitable controller, such as any type of CompactLogix or ControlLogix controller from Allen Bradley. Thus the PLC 319 may be associated with a logic circuit, which may include various hardware and software operable together as an overall 'logic circuit' in which logic of the present disclosure may be implemented.

The logic circuit may be programmable and compatible to various computer devices that include, for example, PCs, workstations, laptops, mobile devices, cell phones, tablets, servers, and the like. For example, and operator 309 may interface with the PLC 319 via a (computer) workstation 316. Although not shown here, in terms of hardware and related architecture, the logic circuit may generally include one or more controllers, memory or data storage, and I/O devices, which may all be operatively communicatively coupled together, including such as circuitry, wiring, pins, and via a local interface (not shown).

As would be apparent to one of skill in the art the local interface may be understood to include, for example, one or more buses or other wired or wireless connections. The local interface may have additional elements, such as controllers, buffers (caches), drivers, repeaters, and receivers, to enable communications. Further, the local interface may include address, control, and/or data connections to enable appropriate communications among the aforementioned components.

The PLC (or sometimes just 'controller') 319 may be a hardware device configured for execution of software (programming, computer readable instructions, etc.), which may be stored (programed thereinto) in a controller memory. The controller 319 may be or include any custom made or commercially available processor, a central processing unit (CPU), a digital signal processor (DSP), or an auxiliary processor among several processors associated therewith.

The PLC 319 memory may include any one or combination of random access memory (RAM), dynamic random access memory (DRAM), static random access memory (SRAM), ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, and so forth. Moreover, the controller memory may incorporate electronic, magnetic, optical, and/or other types of storage media.

Software for the controller 319 may include one or more separate programs, each of which may include an ordered listing of executable instructions for implementing logical functions. Software for the controller 319 may include a suitable operating system (OS), compiler, source code, and/ or one or more applications in accordance with embodiments herein. Software may be an application ("app") that may include numerous functional components for implementing the features and operations of embodiments of the disclosure.

The OS may be configured for execution control of other computer programs, and provides scheduling, input-output, file and data management, memory management, and communication control and related services. In aspects, the app may be suitable for implementation of embodiments herein to all commercially available operating systems.

Software may include an executable program, script, object code, source program, or any other comparable set of instructions to be performed. Software may be written as object oriented programming language, which may have classes of data and methods, or a procedure programming language, which has routines, subroutines, and/or functions. The programming language may include for example Python, HTML, XHTML, Java, ADA, XML, C, C++, C#, Pascal, BASIC, API calls, ASP scripts, FORTRAN, COBOL, Perl, .NET, Ruby, and the like.

In aspects, external computers (and respective programming) may be communicably operable with the PLC 319 (and thus the logic circuit). In operation of the logic circuit, the PLC 319 may: execute software stored within the memory; communicate data to and from the memory; and/or generally control operations of the logic circuit pursuant to the software, especially as it pertains to any and all sensory input data, and outputs.

One of skill would appreciate that although specific instrumentation and wiring are not shown in detail here, that the PLC 319 may be operably engaged with all components, control valves, sensors, etc. of the system 300.

One or more parameters associated with the skid 308 may be monitored, detected, measured, sensed, etc. For example, pressure and temperature of the fluid F1 may be monitored by sensor transmitters, such as at the inlet 315 to the valve 317, and relayed to the PLC 319. This may ensure the fluid F1 has respective properties (e.g., pressure and temperature) within tolerance levels of the equipment of the skid 308. Any tolerance level may be predetermined.

If not within tolerance, the fluid F1 may be diverted out of the skid 308. But provided the tolerance is acceptable, the PLC 317 may be operable to actuate the inlet valve 317 to be positioned or moved whereby inlet piping 312a may in fluid communication with transfer piping 312c.

The transfer piping 312c may be coupled with a separation unit 306. The transfer piping 312c may be coupled with the separation unit 306 via respective flanges and so forth. In a similar manner, transfer piping 312d may be coupled with the inlet valve 317 via connection point 318a, such that fluid transferred through the piping 312d may flow out of the inlet valve 317 via the outlet 318.

As fluid F2 leaves the inlet valve 317 and transfers through the transfer piping 312c, it may be measured for the presence of gas (e.g., percentage gas, gas mass fraction, gas void fraction (GVF), etc.). Thus, the skid 308 may have a gas detection device 326. In embodiments, the gas detection device 326 may be a capacitance transmitter. The capacitance transmitter 326 may be calibrated by measuring pure liquid, and then pure gas (such as air). In this respect the capacitance transmitter 326 may be configured to measure or otherwise sense a percentage of gas present within the fluid F2. The capacitance transmitter 326 may be oriented horizontally.

The gas detection device 326 may be in signal communication with the PLC 319, whereby data may be transmitted therebetween. In the event little to no gas (e.g., GVF) is detected within the fluid F2 by the gas detector 326, such that the amount of gas is below a predetermined threshold, the fluid F2 may be bypassed around the unit 306. For example, the fluid F2 may be bypassed or transferred out of the skid 308 without need for separation. In embodiments, the fluid F2 may be transferred to a liquid meter loop 328 for further processing. The PLC 319 may thus have computer instructions for accomplishing the task, which may include controlling a throttle bypass valve 327. Accordingly, the fluid F2 may flow directly into a liquid meter loop 328. As such the liquid meter loop 328 may be in fluid communication with the inlet valve 317. The liquid meter loop 328 may include multiple components operable together, such as a liquid meter, a conductivity meter, and a water-cut meter.

In the event the gas threshold is exceeded, the fluid F2 may pass the gas detective device 326 and move into the separation unit 306. Although not limited to any particular shape or orientation, the separation unit 306 may have a generally cylindrical shape and vertical orientation (and thus having an axis equivalent or parallel to a vertical axis 325). The separation unit 306 may have an exterior pipe winding 321 therearound.

The exterior (coil) winding 321 may be the form of a plurality of helical (pipe-shaped) loops 323. Although not necessary, the loops 323 may be centralized around the axis 325 such that fluid F2t may circulate therethrough in a downward path. Fluid F2t may be contemplated as the fluid F2 having unstratified flow regimes transitioning to a fluid F3 that has an at least on stratified flow regime. It is noted that in other embodiments, the fluid F2t may flow upwardly through the winding 321, which may be accomplished be a reconfiguration of the associated piping network.

The loops 323 may have a generally curvilinear shape 322 to its flow path. Although not mean to be limited, the exterior winding 321 may have between about 2 loops to about 10 loops, each loop being tantamount to a single 360-degree winding around the vessel portion of the unit 306. The exterior winding may have a varied diameter D1 . . . Di therethrough. In embodiments, the diameter 324 of the loops 323 may remain substantially constant along the length of axis 325 for the entirety of the winding 321. In other embodiments, the diameter 324 of the loops 323 may increase or decrease, either randomly or successively.

In some aspects, it may be desirable to alter the rate of the flow of fluid through the skid 308 (or unit 306), which may occur by increasing or decreasing any diameter 324 of one or more loops 323. For example, decreasing the diameter 324 of a respective loop may increase fluid velocity, leading to greater centrifugal force within the loop 323 (or winding 321), and thus more separation of respective phases.

The configuration of the exterior winding 321 may contribute to shaping the flow regime of the fluid F2. In this respect, the plurality of loops 323 may be provided to develop the increased concentration of a gas (or gas phase) on an inner wall (not shown here) of the exterior winding 321. The fluid F2t may be viewed here as the transition of the fluid F2 from being in an unstratified stated to a fluid F3 having a stratified flow regime. The winding 321, which may be associated with the separation unit 306, may be configured to help restructure the flow regime of the fluid F2 from any type (e.g., bubble flow, annular flow, churn flow) into a stratified flow.

Stratifying the flow, or the stratified flow, may be a way of separating phases in real-time, without having to have residence time. In this respect, the skid 308 may operate with a continuous flow rate of about 0.1 ft/second to about 15 ft/second through the winding 321. The flow rate may be an average bulk velocity of the fluid in a given section of the skid 308. Given the ability to handle such rates, the skid 308 may be useful for measurement and testing of the source 301, even during times of downturn or significantly reduced flow rates. The fluid F2t flowing through the winding 321 may be affected by a combination of forces, such as centrifugal and gravitational, as well as friction.

The outlet of the winding 321 may have a branch transfer piping 312e. The branch transfer piping 312e may be coupled with a separator inlet 342 of the unit 306. Lights or gas may be transferred into the unit 306 via piping 312e. Back pressure via the percentage opening 327 may be used to control flow through the winding 321 and/or into the unit 306.

In embodiments, the separation unit 306 may hold a liquid level (or barrier) to ensure gas is limited or prevented from exiting a liquid outlet (or bottom) 333, of the separation unit 306. As such the liquid phase may be discharged from the outlet 333, and may subsequently be (re)combined at the bypass 327 valve with any fluid that may have bypassed the separation unit 306, resulting in fluid product F4B. The fluid product F4B may transfer or flow into the liquid meter loop 328.

At the same time gas may be removed from fluid, either through the loops 323 or inside the unit 306 itself. Gas F4A, including any removed via separation, may exit the unit 306 through a top gas outlet 334. The gas F4A may be transferred into or through a gas meter loop 335. The gas meter loop 335 may include a number of (sub)components operable together and in conjunction with others of the skid 308. For example, the gas meter loop 335 may include a gas meter 336, such as gas Coriolis meter. The gas meter 336 may be arranged in any suitable fashion or orientation, such as vertical or horizontal. As shown here, the gas F4A may flow downward through the gas meter loop 335 to or past a gas valve 337. Thus the gas meter loop 336 may include the gas valve 337.

The gas valve 337 may be configured to throttle, and thereby maintain liquid level in the separation unit 337. Liquid level of the separation unit 306 may be measured (monitored, sensed, etc.) by suitable measurement instrumentation 338. In an embodiment, the liquid level may be measured by a guided wave radar level transmitter, which may be configured to send level information to a PLC operable to controls the gas valve 337. The PLC 319 may be operable and configured to control the gas valve 337.

In an embodiment of operation, if the liquid level increases beyond a first predetermined level point in the separation unit 306, the gas valve 337 may start to throttle closed, which may result in building pressure in the separation unit 306. The increase in pressure within the unit may begin to push or otherwise urge the liquid level down out through the liquid outlet 333. In the event the liquid level decreases below a second predetermined level point in the separation unit, the gas valve 337 may begin to throttle open, which may result in the release of pressure through the gas outlet 334. This may allow the liquid level to increase.

As mentioned, the liquid meter loop 328 may include a meter, such as a liquid meter 329. The liquid meter 329 may be a volumetric flow meter. The liquid meter 329 may be a liquid Coriolis meter. The difference between a gas Coriolis meter and a liquid Coriolis meter may be contemplated as having little difference subject to meter and software configuration. Thus gas meter 336 and liquid meter 329 may be interchangeable subject to hardware and software configuration. The liquid meter 329 may be arranged in a horizontal orientation. In this sense, fluid F4B (which may be part or all of fluid F3 flowing through valve 327) may flow through the meter 329. The fluid F4B may be directed upward and therethrough.

The liquid meter 329 may have an associated drive gain. The drive gain of the meter 329 may be monitored as a point of secondary control to the bypass valve 327. If a high percentage of drive gain above a predetermined threshold is recorded, this may indicate the presence of undesired gas flowing to the liquid meter 329. Accordingly, the PLC 319 may be configured with switch control, whereby control of the bypass valve 327 may be switched from the gas detector 326 to the liquid meter 329. The skid 308 may thus be configured for the bypass valve 327 to close in a proportional manner to the amount of drive gain (percentage) determined. Thus, any undesired drive gain of the liquid meter 329 may be restored. The control of the bypass valve 328 may be switched (back) to the gas detector 326.

As fluid flow through the liquid meter and is measured, the resultant measured fluid F4B may continue to flow through the liquid meter loop (including upwardly) to a second liquid meter 330. In an embodiment the liquid meter loop 328 may include the second liquid meter 330. The second liquid meter 330 may be configured to determine another parameter associated with liquid flow in the skid 308. Although not meant to be limited, the second liquid meter may be a conductivity transmitter configured to measure the conductivity of the fluid F4B passing therethrough. The fluid F4B may be measured in applicable units, such as millisiemens for conductivity, and have an associated tolerance range.

The fluid F4B may continue through the liquid meter loop 328, and (upward) into a third liquid meter 331. As such, the liquid meter loop 328 may include the third liquid meter 331. The third liquid meter 331 may be a liquid cut meter. The third liquid meter 331 may be a water cut meter configured to give a reading or signal in a manner, whereby a percentage of water and non-water (e.g., oil) and water flowing through the meter 331 may be determined in real time without separation of the water and non-water constituents. The third liquid meter 331 may be configured to use microwave resonance to detect changes of dielectric permittivity to calculate the percentage of constituents. There may be a water cut temperature transmitter 344.

Of significance, measurement data from respective meters (and associated sensors and instrumentation) may be transmitted to the PLC 319. Measurement data may include, but not be limited to, density (including mixed density of an oil-water mixture) and/or volume (such as from the liquid meter 329), conductivity (such as from the second liquid meter 330), pressure (such as from a pressure sensor transmitter 337), temperature (such as from temperature sensor transmitter 344), etc., any of which may be transmitted to the PLC 319 from each respective device. The PLC 319 may then process and/or send combined data to the third liquid meter 331. This may beneficially result in real time compensation to the values provided by the third liquid meter 331, and compensate for any liquid property changes.

As fluid F4B exits the liquid meter loop 328, the fluid may transfer (such as downward through piping) to the outlet 318, and out of the inlet valve 317. Gas F4A may also be transferred out of the inlet valve 317. As shown, gas F4A may exit the unit via gas exit transfer piping 312f. The gas exit transfer piping 312f may be in fluid communication with exit conduit 339. There may be a gas control valve 343 associated therewith for controlling gas flow.

Gas F4A may transfer to and through gas exit conduit 339. The gas exit conduit 339 may be tied (connected, etc.) between the gas meter loop 335 and the exit transfer piping 312d. As such, the outlet 318 of the skid 308 and the gas meter loop 335 may be, directly or indirectly, in fluid communication. In this respect, gas, separated or otherwise, may be (re)injected into the fluid F4B as it exits the outlet 318 (see injection point 340). As such, the fluid F5, which may be liquid (re)combined with gas, may exit the skid 308. In other embodiments, the gas F4A may be (re)combined at other points, such as at tie-in (flange) 318a, along transfer line 312d, or other suitable point.

It is noted that while the testing system 300 may be referred to or include part of a 'skid' for simplicity, components of the skid need not be skid mounted. As such, components or units described herein may be part of an overall treatment (such as separating, testing, combinations, etc.) system, such as system 300. While it need not be exactly the same, system 300 may include various features and components like that of other systems or units described herein, and thus components thereof may be duplicate or analogous.

Figure 4:
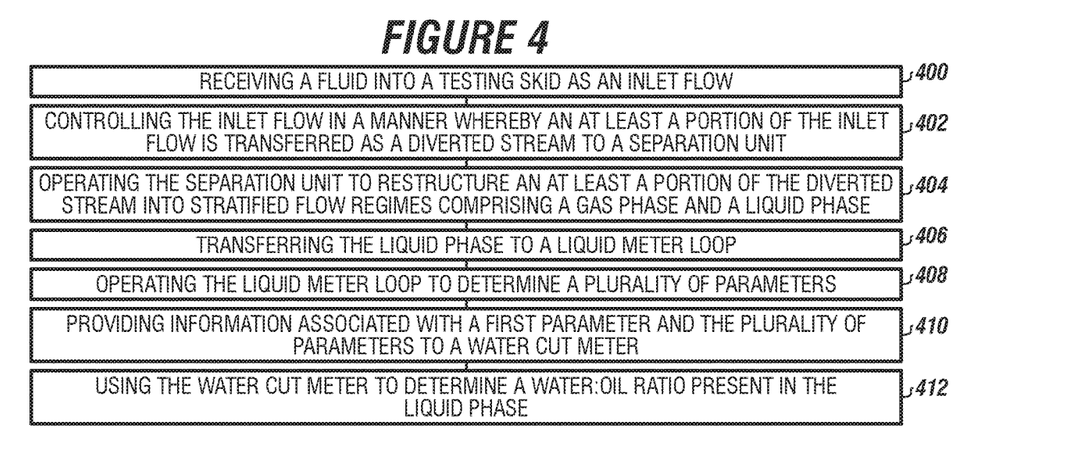
FIG. 4 shows steps for a method of processing a fluid according to embodiments of the disclosure.

Referring now to FIG. 4, an overview of steps for a method of processing a fluid, in accordance with embodiments disclosed herein, is shown. Even if not shown in detail, the method briefly described herein with regard to FIG. 4 may be applicable to systems also described herein in the sense that to perform the method, some or all of systems 200, 300, etc. may be used.

The method for processing a fluid that may include the step of receiving the fluid into a testing skid as an inlet flow 400. The fluid may be a multi-phase fluid. The method may include controlling the inlet flow in a manner whereby an at least a portion of the inlet flow is transferred as a diverted stream to a separation component 402. The separation component may be associated with the testing skid. The separation component may be a component or subcomponent of a separation unit. The separation component may be a coil winding, which may be associated with the separation unit.

The method may include determining a first parameter of the diverted stream. The method may include using the separation component to restructure an at least a portion of the diverted stream into stratified flow regimes comprising one or both of a gas phase and a liquid phase 404. The method may include transferring the liquid phase from the separation component to a liquid meter loop 406. The meter loop may include a flow meter and a water cut meter.

The method may include operating the liquid meter loop to determine a plurality of parameters 408. In aspects, a flow rate and a percent of water of the liquid phase may be determined.

The method may include providing information associated with a first parameter and the plurality of parameters to the water cut meter 410. The method may further include using the water cut meter to determine a water:oil ratio present in the liquid phase 412. The method may include discharging the liquid phase from the testing skid.

After stratifying, the (separated) gas phase may include greater than 99% by weight gas. The (separated) liquid phase may include greater than 99% by weight liquid. There may be an average bulk residence time of the at least a portion of the diverted stream in the separation unit of 1 second to 2 minutes. In embodiments, the retention time may be less than 5 minutes.

In aspects, the liquid meter may be arranged vertically. Accordingly, the liquid phase may enter a bottom of the liquid meter and exit a top of the liquid meter.

The method may include reinjecting the gas phase into the liquid phase to form a recombined stream that is then subject to the discharging step. In aspects, the separation component may be an external winding helically wound in a horizontal orientation. The external winding may include between 2 to 10 coil loops. The external winding may be formed around or be part of a separation unit.

The diverted stream may have an average bulk fluid velocity through the separation component between 0.1 feet per second to 15 feet per second.

Advantages

Embodiments of the disclosure advantageously provide for improved fluid treatment useable with a wide array of applications.

Beneficially a source of a fluid, such as a wellbore, may be evaluated in real time with inline separation and measurement. No retention time is needed. Changes in the fluid may be evaluated and compensated for with ease.

As retention time is not needed (and hence large vessels are not needed), embodiments herein provide for smaller footprint, and lower overall costs. Embodiments herein do not require separation of oil and water, which is a benefit to the environment as oil/water separation is usually accomplished with energy and/or chemical consumption.

Since separation occurs in a substantially complete or complete manner, greater accuracy may be obtained.

Other advantages may be derived from being able to accommodate and handle significant turndown rates, which may result from depletion. That is, normal test/measurement occurs with huge retention vessels that cannot accommodate testing/measuring during turndown. Turndown may be encountered when will production dips. Embodiments herein provide for ability to handle even rates as low as 2 barrels per day, and even up to 5000 barrels per day. In comparison, a traditional separator configured to handle 5000 barrels per day would need minimum flow typically in excess of about 500 barrels in order to properly function.

Embodiments of the disclosure advantageously provide for new and innovative systems, hardware, software, and related methods, for treating a fluid. One or more embodiments herein may be retrofitted to existing equipment. Embodiments of the disclosure advantageously provide for new and durable equipment units useable separately or together in a wide range of onshore and offshore environments where fluid treatment is desirous.

While embodiments of the disclosure have been shown and described, modifications thereof can be made by one skilled in the art without departing from the spirit and teachings of the disclosure. The embodiments described herein are exemplary only, and are not intended to be limiting. Many variations and modifications of the disclosure presented herein are possible and are within the scope of the disclosure. Where numerical ranges or limitations are expressly stated, such express ranges or limitations should be understood to include iterative ranges or limitations of like magnitude falling within the expressly stated ranges or limitations. The use of the term "optionally" with respect to any element of a claim is intended to mean that the subject element is required, or alternatively, is not required. Both alternatives are intended to be within the scope of any claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the preferred embodiments of the disclosure. The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

What is claimed is:

1. A method for processing a fluid comprising:
receiving the fluid into a testing skid as an inlet flow, the fluid comprising a multi-phase fluid produced from a well;
controlling the inlet flow in a manner whereby an at least a portion of the inlet flow is transferred as a diverted stream to a separation component associated with the testing skid;
determining a first parameter of the diverted stream;
using the separation component to restructure an at least a portion of the diverted stream into stratified flow regimes comprising a gas phase and a liquid phase;
transferring the liquid phase from the separation component to a liquid meter loop comprising a flow meter and a water cut meter;
operating the liquid meter loop to determine a plurality of parameters, whereby a flow rate and a percent of water of the liquid phase are determined;
providing information associated with a first parameter and the plurality of parameters to the water cut meter;
using the water cut meter to determine a water:oil ratio present in the liquid phase; and
discharging the liquid phase from the testing skid.

2. The method of claim 1, wherein the gas phase comprises greater than 99% by weight gas, wherein the liquid phase comprises greater than 99% by weight liquid.

3. The method of claim 1, wherein an average bulk residence time of the at least a portion of the diverted stream in the separation unit is less than 5 minutes.

4. The method of claim 1, wherein the liquid meter is arranged vertically, whereby the liquid phase enters a bottom of the liquid meter and exits a top of the liquid meter.

5. The method of claim 1, the method further comprising reinjecting the gas phase into the liquid phase to form a recombined stream that is then subject to the discharging step.

6. The method of claim 1, wherein the separation component comprises an external winding helically wound in a horizontal orientation, and further comprising between 2 to 10 coil loops formed around a separation unit.

7. The method of claim 1, wherein the diverted stream has an average bulk fluid velocity through the separation component between 0.1 feet per second to 15 feet per second.

8. A method for processing a fluid comprising:
receiving the fluid into a testing skid as an inlet flow, the fluid comprising a multi-phase fluid transferred from a fluid source;
controlling the inlet flow in a manner whereby an at least a portion of the inlet flow is transferred as a diverted stream to an external winding associated with the testing skid, the external winding comprising between 2 to 10 coil loops disposed around a separator vessel;
determining a first parameter of the diverted stream;
using the separation component to restructure an at least a portion of the diverted stream into flow regimes comprising a gas phase and a liquid phase;
transferring the liquid phase from a winding outlet of the external winding to a liquid meter loop comprising a flow meter and a water cut meter;
operating the liquid meter loop to determine a plurality of parameters, whereby a flow rate and a percent of water of the liquid phase are determined;
providing a set of data associated with a first parameter and the plurality of parameters to the water cut meter;
using the water cut meter to determine a water:oil ratio present in the liquid phase; and
discharging the liquid phase from the testing skid.

9. The method of claim 8, wherein the set of data is calculated by a programmable logic controller, wherein the liquid phase comprises greater than 99% by weight liquid, and wherein the determining the first parameter step pertains to using a gas detector device configured to determine a percentage of gas within the diverted stream.

10. The method of claim 9, wherein the liquid meter is oriented vertically, whereby the liquid phase enters a bottom of the liquid meter and exits a top of the liquid meter, and wherein the gas detector device is oriented horizontally.

11. The method of claim 10, the method further comprising reinjecting the gas phase into the liquid phase, after the liquid phase is transferred from the liquid meter loop, to form a recombined stream that is then subject to the discharging step.

12. The method of claim 11, wherein the external winding is wound in a horizontal orientation.

13. The method of claim 12, wherein the diverted stream has an average bulk fluid velocity through the external winding between 0.1 feet per second to 15 feet per second.

14. A method for processing a fluid comprising:
receiving the fluid into a testing skid as an inlet flow, the fluid comprising a multi-phase fluid transferred from a fluid source;
controlling the inlet flow in a manner whereby an at least a portion of the inlet flow is transferred as a diverted stream to an external winding associated with the testing skid, the external winding comprising between 2 to 10 coil loops wound horizontally around a separator vessel;
determining a first parameter of the diverted stream;
using the external winding to restructure an at least a portion of the diverted stream into flow regimes comprising a gas phase and a liquid phase;
transferring the liquid phase from a winding outlet of the external winding to a liquid meter loop comprising a flow meter and a water cut meter;
operating the liquid meter loop to determine a plurality of parameters, whereby a flow rate and a percent of water of the liquid phase are determined;
providing a set of data associated with a first parameter and the plurality of parameters to the water cut meter;
using the water cut meter to determine a water:oil ratio present in the liquid phase; and
discharging the liquid phase from the testing skid, wherein the set of data is calculated by a programmable logic controller, wherein the liquid phase comprises greater than 99% by weight liquid, wherein the determining the first parameter step pertains to using a gas detector device configured to determine a percentage of gas within the diverted stream, and wherein the diverted stream has an average bulk fluid velocity through the separation component between 0.1 feet per second to 15 feet per second.

15. The method of claim 14, wherein the liquid meter is oriented vertically, whereby the liquid phase enters a bottom of the liquid meter and exits a top of the liquid meter, and wherein the gas detector device is oriented horizontally.

* * * * *